United States Patent [19]

Clossick

[11] Patent Number: 4,815,476
[45] Date of Patent: Mar. 28, 1989

[54] BIOPSY FORCEPS WITH LOCKING HANDLE

[75] Inventor: James P. Clossick, Miami Lakes, Fla.
[73] Assignee: Cordis Corporation, Miami, Fla.
[21] Appl. No.: 172,773
[22] Filed: Mar. 28, 1988
[51] Int. Cl.$^4$ .............................................. A61B 10/00
[52] U.S. Cl. ..................................... 128/751; 128/321
[58] Field of Search ............... 128/305, 321, 322, 323, 128/324, 749, 750, 751, 752, 753, 754

[56] References Cited

U.S. PATENT DOCUMENTS 3,995,619  12/1976  Glatzer ................................. 128/749
4,646,751  3/1987  Maslanka ............................. 128/321

Primary Examiner—Edward M. Coven
Assistant Examiner—Randy Citrin
Attorney, Agent, or Firm—Henry W. Collins; Thomas R. Vigil

[57] ABSTRACT

A biopsy forceps device comprises a handle portion an elongate flexible hollow body portion having a proximal end coupled to the handle portion and a distal end. A forceps assembly is coupled to the distal end and includes a pair of forceps. A stylet control wire in the body portion is coupled to the pair of forceps at the distal end of the body portion. A locking hub assembly is coupled between the handle portion and the proximal end of the body around the stylet/control wire and includes a locking hub and locking means for locking the stylet/control wire in an axial position thereof to the locking hub assembly relative to the body portion upon rotation of the locking hub.

7 Claims, 2 Drawing Sheets

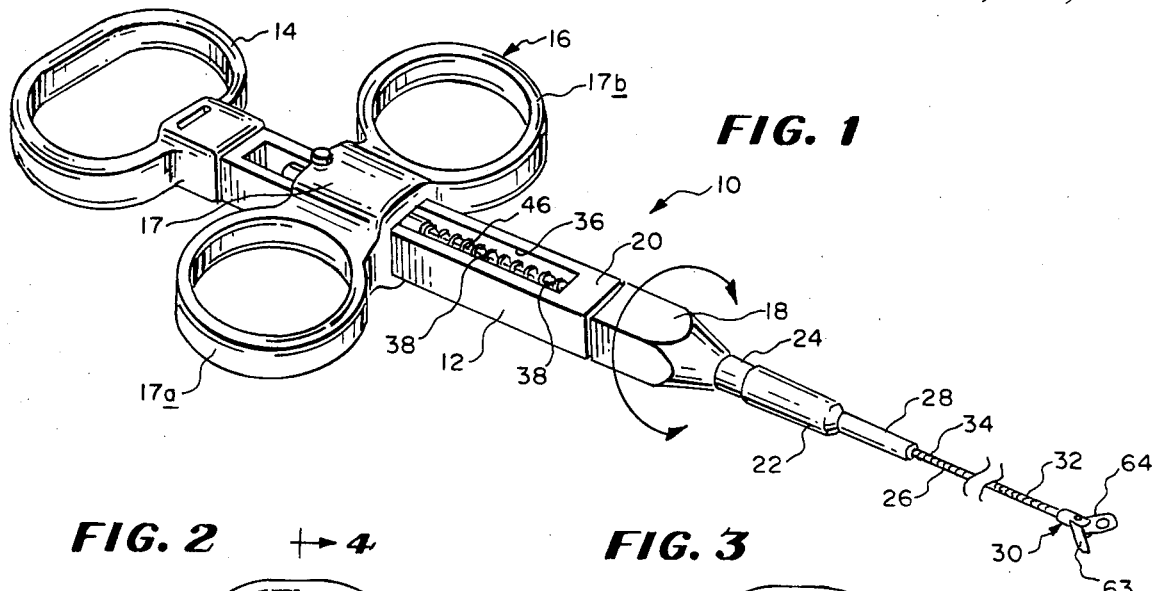
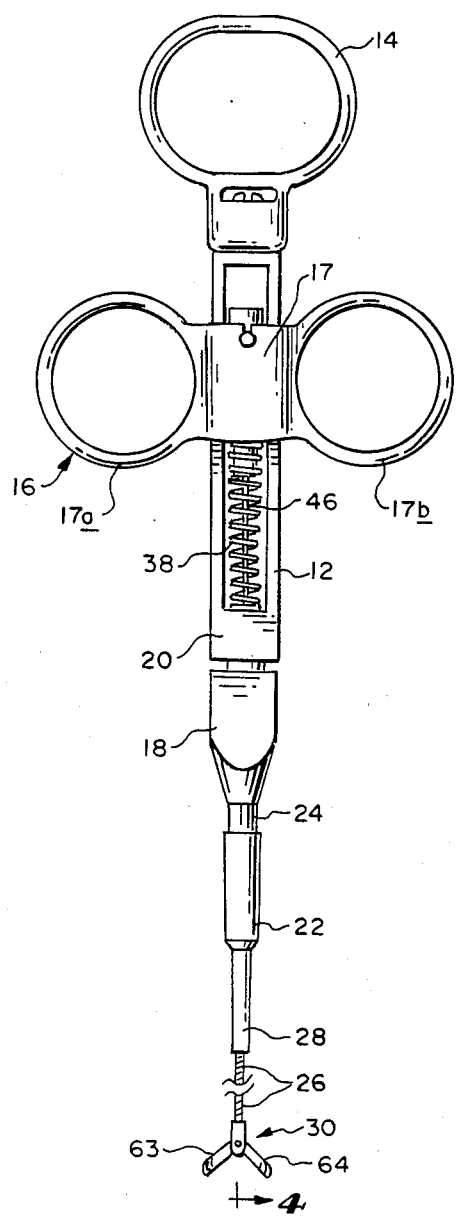
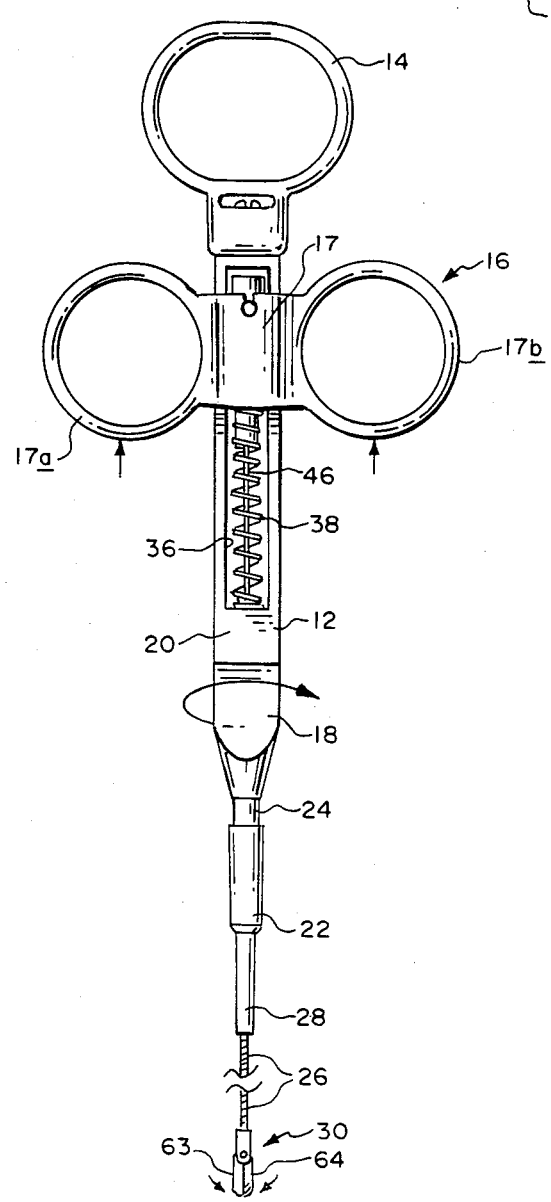
FIG. 1
FIG. 2
FIG. 3

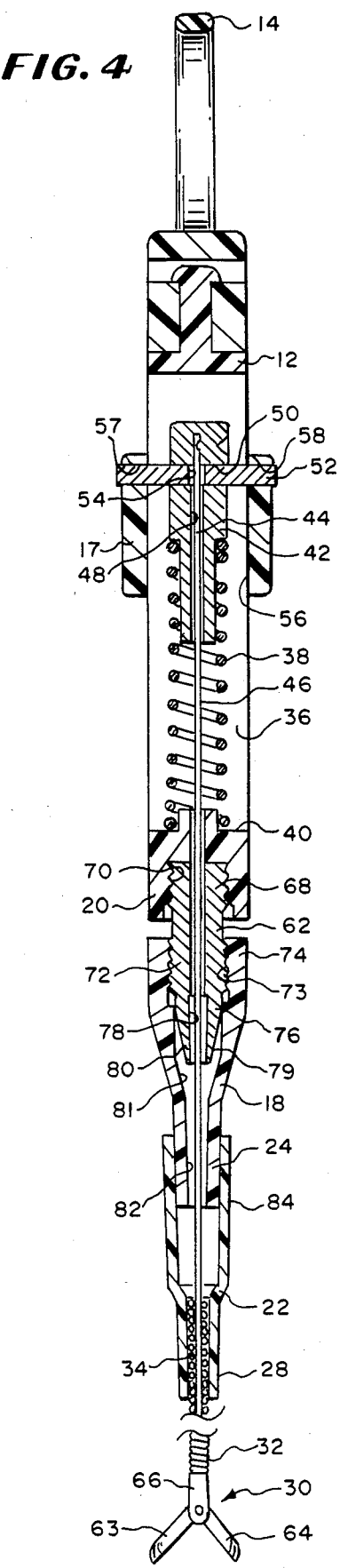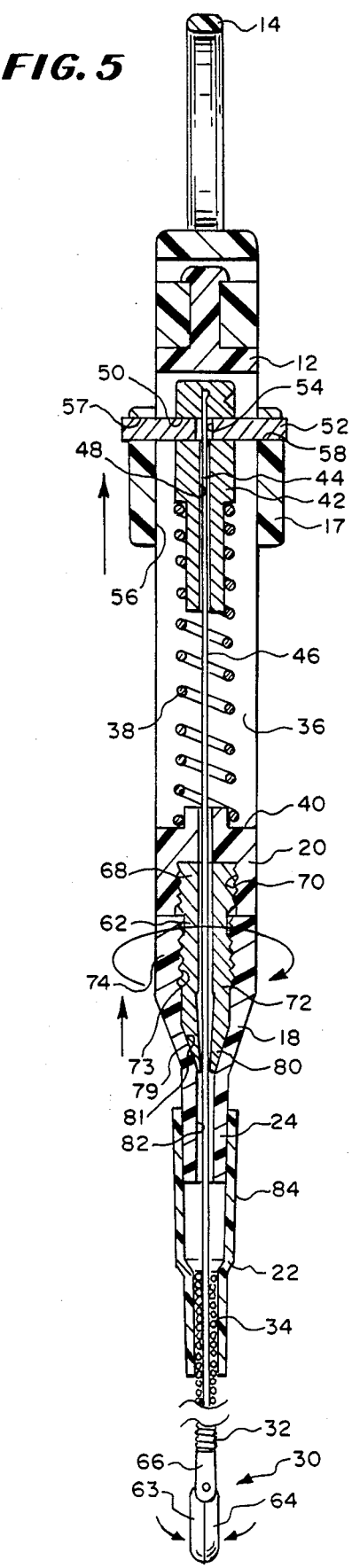

BIOPSY FORCEPS WITH LOCKING HANDLE

FIELD OF THE INVENTION

The present invention relates to a biopsy forceps device and more particularly to such a device which has a mechanism for releasably locking the axial position of a stylet/control wire connected to the proximal end of a pair of pivotably mounted forceps relative to a coil spring guidewire in which it is received.

DESCRIPTION OF THE PRIOR ART

Heretofore various biopsy forceps devices have been proposed. Such a device includes a handle portion slidably mounting a trigger member thereon on, an elongate coil spring guidewire connected to the handle portion at its proximal end and having a pair of forceps mounted to its distal end, and a stylet/control wire received within the coil spring guidewire and connected at its proximal end to the trigger and at its distal end to the pair of forceps.

Forward movement of the trigger causes the stylet/control wire to move the pair of forceps to an open position and rearward movement of the trigger causes the pair of forceps to move to a closed position.

It is desirable to maintain the pair of forceps closed when inserting or withdrawing the biopsy forceps device into or out of a blood vessel in a body.

As will be described in greater detail hereinafter, the biopsy forceps device of the present invention differs from prior devices by providing a simple mechanism, operable upon rotation of a part thereof, to grip and lock the stylet/control wire in an axial position relative to the coil spring guidewire for maintaining the pair of forceps in a closed position while inserting or withdrawing the device into or out of a blood vessel.

SUMMARY OF THE INVENTION

According to the present invention there is provided a biopsy forceps device comprising
a handle portion;
an elongate flexible hollow body portion having a proximal end coupled to the handle portion and a distal end;
a forceps assembly coupled to the distal end and including a pair of forceps;
a stylet/control wire in the body portion coupled to a pair of forceps at the distal end of the body portion; and
a locking hub assembly coupled between the handle portion and the proximal end of the body portion and around the stylet/control wire and including a locking hub and locking means for locking the stylet/control wire in an axial position thereof to the locking hub assembly relative to the body portion upon rotation of the locking hub.

BRIEF DESCRIPTION OF THE DRAWINGS

FIG. 1 is a perspective view of a biopsy forceps device including a locking hub or handle and a pair of forceps constructed according to the teachings of the present invention.

FIG. 2 is a plan view of the biopsy forceps device shown in FIG. 1 and shows an unlocked position of the locking hub and an open position of the forceps.

FIG. 3 is a plan view similar to the view shown in FIG. 2 and shows the locking hub in a locked position and the forceps in a closed position.

FIG. 4 is a longitudinal sectional view of the biopsy forceps device shown in FIG. 2 where the forceps are open and the locking hub is unlocked.

FIG. 5 is a longitudinal sectional view of the biopsy forceps device shown in FIG. 3 where the forceps are closed and the locking hub is locked.

DESCRIPTION OF THE PREFERRED EMBODIMENT

Referring now to the drawings in greater detail, there is illustrated in FIG. 1 a biopsy forceps device 10 including a handle portion 12 having a thumb receiving end ring 14, a FIG. 8 shaped trigger 16 having a hollow middle portion 17 slidably received over and on the handle portion 12, and opposed finger receiving rings 17a and 17b, a locking hub or handle 18 mounted on a distal end 20 of the handle portion 12, a sleeve 22 extending from a distal end 24 of the locking hub 18, and a coil spring guidewire 26 extending from a distal end 28 of the sleeve 22. Most of the length of the coil spring guidewire 26 is broken away in the Figures and a forceps assembly 30 is mounted to a distal end 32 of the coil spring guidewire 26.

The locking hub 18 is coupled by the stiff but flexible sleeve 22 to a proximal end 34 of the coil spring guidewire 26.

The handle portion 12 is of conventional construction and has a longitudinally extending transverse slot 36 therethrough in which is positioned a spring 38 which extends between a forward wall 40 of the slot 36 and a plug member 42 (FIG. 4) connected to the trigger 16. Connected to the plug member 42 of the trigger 16 is a proximal end 44 of an operating stylet or control wire 46. More specifically, as shown in FIGS. 4 25 and 5, the proximal end 44 of the stylet or control wire 46 is received in a bore 48 of the plug member 42 which also has a transverse bore 50 therein which receives a pin 52 that has a bore 54 extending transversely therethrough.

In the assembly of the handle portion 12, the middle body portion 17 of the trigger 16, which has a generally square-in-cross-section opening 56 therethrough, is received over the generally square-in-cross-section handle portion 12. Then pin 52 is extended through holes 57, 58 in opposite sides of the hollow body 17 and the bore 50 in the plug member 42.

After the plug member 42 is positioned within the slot 36 and within the body 17 of the trigger 16, and the transverse bore 50 in the plug member 42 is aligned with the two opposed holes 57, 58 in the body 17. Next, the pin 52 is inserted through the aligned holes 57, 58 and the bore 50 to place the pin 52 in the plug member 42 with the transverse bore 54 in the pin 52 in alignment with the longitudinal bore 48 in the plug member 42 as shown in FIGS. 4 and 5. Then, the proximal end 44 of the control wire 46 is inserted all the way into the bore 48 through the bore 54 in the pin 52 until it bottoms at the bottom of the bore 48 in the plug member 42. The plug member 42 is then swaged to fix the proximal end 44 of the control wire 46 in the plug member 42.

As shown, the spring 38 is received over a distal end 60 of the plug member 42 and extends between the plug member 42 and the forward wall 40 of the slot 36.

The stylet/control wire 46 extends out of the handle portion 12 and through a collet member 62, through the locking hub 18, the sleeve 22, and the coil spring guidewire 26 to the forceps assembly 30 where it is connected to the rear end of a pair of forceps 63, 64 of the forceps assembly 30 pivotally mounted to a body 66 of the forceps assembly 30, which body 66 is connected to the distal end 32 of the coil spring guidewire 26.

The collet member 62 has a proximal portion 68 threadably received in a threaded bore 70 in the distal end 20 of the handle portion 12 and a central portion 72' which is threaded and received in a threaded bore 73 in proximal end 74 of the locking hub 18. The collet member 62 has a conical, longitudinally split, forward end portion 76 which can have 2, 3 or 4 slots 78 therein. Preferably the forward end portion 76 has a generally conical outer surface 79 and four longitudinal slots 78 extending therethrough only one of which is shown. With this construction, the forward end portion 76 has two, three or (preferably) four, finger portions 80 between the slits which can be flexed to grip the control wire 46 in the manner described below.

As shown, the locking hub 18 has a conically shaped cavity 81 therein into which the split forward end 76 of the collet member 62 is received. The cavity 81 has a conical side wall adapted to engage the collet member 62 and the locking hub 18 has a bore 82 in the distal end 24 thereof communicating between the cavity 81 and the interior of the sleeve 22. The proximal end 84 of the sleeve 22 is received over the distal tubular end 24 of the locking hub 18. Then, the reduced-in-diameter distal end 28 of the sleeve 22 is received over and fixed to the proximal end 34 of the coil spring guidewire 26.

The forward, conically shaped end 76 of the collet member 62 20 is shown with two opposite slots 78 therein. However, it is to be understood that it can be provided with four opposed slots 78 each 90° away from the other slots.

As shown in FIGS. 2 and 4, once the coil spring guidewire 26 of the biopsy forceps device 10 is inserted into a body cavity 81, such as through a blood vessel to a chamber of the heart, the forceps 63, 64 are opened by moving the trigger 16 forward. Then the opened pair of forceps 63 and 64 are positioned adjacent body tissue in the body cavity 81.

Next, as shown in FIGS. 3 and 5, the trigger 16 is pulled rearwardly to pull the stylet control wire 46 to cause the pair of forceps 63 and 64 to close and capture and cut off a piece of body tissue.

According to the teachings of the present invention, in order to facilitate the maintaining of the forceps assembly 30 closed after the trigger 16 is moved rearwardly, the locking hub 18 is rotated from the position shown in FIG. 3 to the position shown in FIG. 5 to cause the proximal end 74 of the locking hub 18 to be threaded rearwardly over the end portion 72 of the collet member 62. This movement causes the finger portions 80 in the split forward end 76 of the collet member 62 to be engaged by the wall of the cavity 81 and moved radially inwardly of the cavity 81 which forces the finger portions 80 of the forward end 76 of the collet member 62 to flex inwardly toward each other and toward the stylet control wire 46 so as to grip the stylet control wire 46 and lock it in place thereby to lock the pair of forceps 63 and 64 in place, as shown in FIG. 5.

Once this has been achieved, the coil spring guidewire 26 of the biopsy forceps device 10 can then be withdrawn from the blood vessel with the opening of the pair of forceps 63 and 64 being prevented by the locked position of the stylet control wire 46, to open.

This ensures that the biopsy specimen will not be lost and also that premature opening of the pair of forceps 63 and 64 is prevented, which could possibly cause damage to the walls of the vessels through which the coil spring guidewire 26 is withdrawn.

Principally, the biopsy forceps device 10 provides a simple and efficient means for locking the pair of forceps 63 and 64 in a specimen-captured-closed-position by locking the stylet control wire 46 after it has been moved rearwardly to close the pair of forceps 63 and 64 about a tissue specimen. From the foregoing description, it will be apparent that modifications can be made to the biopsy forceps device and locking hub thereof of the present invention without departing from the teachings of the present invention. Accordingly, the scope of the invention is only to be limited as necessitated by the accompanying claims.

I claim:

1. A biopsy forceps device comprising
a handle portion;
an elongate flexible hollow body portion having a proximal end coupled to said handle portion and a distal end;
a forceps assembly coupled to said distal end and including a pair of forceps;
a stylet/control wire in said body portion coupled to said pair of forceps at the distal end of said body portion; and
a locking hub assembly coupled between said handle portion and said proximal end of said body portion and around said stylet/control wire and including a locking hub and locking means for locking said stylet/control wire in an axial position thereof to said locking hub assembly relative to said body portion upon rotation of said locking hub.

2. The biopsy forceps device of claim 1 wherein said locking means includes a collet member in said locking hub.

3. The biopsy forceps device of claim 2 wherein said locking hub has a generally cylindrical cavity portion therein and a generally conical cavity portion therein.

4. The biopsy forceps device of claim 3 wherein said collet member has a split generally conical distal end portion with fingers defined between each pair of adjacent splits and said generally conical distal end portion and said locking hub are movable relative to each other to cause said generally conical cavity portion to engage said generally conical distal end portion for urging said fingers against said control wire to grip and hold said control wire in said locking hub assembly.

5. The biopsy forceps device of claim 4 wherein said generally conical distal end portion has four splits therein equally spaced around said distal end portion and defining therebetween four fingers in said collet member distal end portion.

6. The biopsy forceps device of claim 4 wherein said generally cylindrical cavity portion of said hub is threaded and said collet member has a threaded outer surface which is received in said threaded cavity portion of said hub.

7. The biopsy forceps device of claim 6 wherein said collet member has a proximal end portion which is threaded and which is threadably received in a threaded bore in said handle portion and fixed therein whereby said locking hub can be rotated on said threaded outer surface of said collet member to cause the wall of said generally conical cavity portion to be moved against said split conical distal end portion to urge said fingers against said stylet-control wire to lock said wire in a desired axial position thereof to said locking hub assembly.

* * * * *